United States Patent
Chen

(10) Patent No.: US 10,524,676 B2
(45) Date of Patent: Jan. 7, 2020

(54) APPARATUS AND METHOD FOR DETERMINING A HEALTH PARAMETER OF A SUBJECT

(71) Applicant: BOE TECHNOLOGY GROUP CO., LTD., Beijing (CN)

(72) Inventor: Ruisi Chen, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 349 days.

(21) Appl. No.: 15/542,162

(22) PCT Filed: Jan. 25, 2017

(86) PCT No.: PCT/CN2017/072638
§ 371 (c)(1),
(2) Date: Jul. 7, 2017

(87) PCT Pub. No.: WO2017/185846
PCT Pub. Date: Nov. 2, 2017

(65) Prior Publication Data
US 2018/0206749 A1    Jul. 26, 2018

(30) Foreign Application Priority Data

Apr. 29, 2016 (CN) .......................... 2016 1 0282810

(51) Int. Cl.
*A61B 5/024*    (2006.01)
*A61B 5/11*    (2006.01)
(Continued)

(52) U.S. Cl.
CPC .......... *A61B 5/02438* (2013.01); *A61B 5/024* (2013.01); *A61B 5/02405* (2013.01);
(Continued)

(58) Field of Classification Search
None
See application file for complete search history.

(56) References Cited

U.S. PATENT DOCUMENTS

| 5,749,366 A | 5/1998 | Odagiri et al. |
| 2014/0213858 A1 | 7/2014 | Presura et al. |

(Continued)

FOREIGN PATENT DOCUMENTS

| CN | 103284705 A | 9/2013 |
| CN | 103781414 A | 5/2014 |

(Continued)

OTHER PUBLICATIONS

First Office Action in the Chinese Patent Application No. 201610282810.X, dated Jul. 25, 2018; English translation attached.
(Continued)

*Primary Examiner* — Eric F Winakur
*Assistant Examiner* — Marjan Fardanesh
(74) *Attorney, Agent, or Firm* — Intellectual Valley Law, P.C.

(57) ABSTRACT

The present application discloses an apparatus for determining a health parameter of a subject. The apparatus includes one or more biometric sensors configured to detect one or more biometric signals of the subject; a memory; and at least one processor. The memory stores computer-executable instructions for controlling the at least one processor to receive the one or more biometric signals from the one or more biometric sensors; classify physiological state of the subject as one of a plurality of physiological states comprising at least a first physiological state and a second physiological state based on the one or more biometric signals, the first physiological state being different from the second physiological state; and calculate the health parameter of the subject using one of a plurality of algorithms comprising at least a first algorithm corresponding to the first physiological state and a second algorithm corresponding to the second physiological state.

5 Claims, 4 Drawing Sheets

(51) Int. Cl.
*A61B 5/00* (2006.01)
*A61B 5/04* (2006.01)
(52) U.S. Cl.
CPC .......... *A61B 5/1123* (2013.01); *A61B 5/7257* (2013.01); *A61B 5/04014* (2013.01); *A61B 5/04017* (2013.01); *A61B 5/721* (2013.01)

(56) References Cited

U.S. PATENT DOCUMENTS

| | | |
|---|---|---|
| 2015/0088013 A1 | 3/2015 | Nakamura |
| 2016/0098081 A1 | 4/2016 | Takahashi et al. |
| 2017/0164851 A1* | 6/2017 | Takahashi .......... A61B 5/02438 |

FOREIGN PATENT DOCUMENTS

| | | | |
|---|---|---|---|
| CN | 104161505 | A | 11/2014 |
| CN | 104203090 | A | 12/2014 |
| CN | 104739399 | A | 7/2015 |
| CN | 105476620 | A | 4/2016 |
| EP | 0733340 | A1 | 9/1996 |
| JP | 2011098002 | A | 5/2011 |

OTHER PUBLICATIONS

International Search Report & Written Opinion dated Apr. 28, 2017, regarding PCT/CN2017/072638.

\* cited by examiner

APPARATUS AND METHOD FOR DETERMINING A HEALTH PARAMETER OF A SUBJECT

CROSS-REFERENCE TO RELATED APPLICATION

This application is a national stage application under 35 U.S.C. § 371 of International Application No. PCT/CN2017/072638 filed Jan. 25, 2017, which claims priority to Chinese Patent Application No. 201610282810.X, filed Apr. 29, 2016, the contents of which are incorporated by reference in the entirety.

TECHNICAL FIELD

The present invention relates to medical devices, more particularly, to an apparatus and a method for determining a health parameter of a subject.

BACKGROUND

Various types of medical devices have been developed for determining medical information of a subject, e.g., a human. For example, various heart rate detectors are now available for conveniently determining a heart rate of a subject. Some of these medical devices have been made in miniaturized forms, e.g., a portable medical device. In particular, medical devices for determining health information and medical information have been incorporated into various wearable apparatus such as glasses, gloves, watches, apparel, shoes, and hats.

SUMMARY

In one aspect, the present invention provides an apparatus for determining a health parameter of a subject, comprising one or more biometric sensors configured to detect one or more biometric signals of the subject; a memory; and at least one processor; wherein the one or more biometric sensors, the memory, the at least one processor are communicatively connected with each other; the one or more biometric signals comprises at least a pulse wave signal of the subject; and the memory stores computer-executable instructions for controlling the at least one processor to receive the one or more biometric signals from the one or more biometric sensors; classify physiological state of the subject as one of a plurality of physiological states comprising at least a first physiological state and a second physiological state based on the one or more biometric signals, the first physiological state being different from the second physiological state; and calculate the health parameter of the subject using one of a plurality of algorithms comprising at least a first algorithm corresponding to the first physiological state and a second algorithm corresponding to the second physiological state, the first algorithm being different from the second algorithm.

Optionally, the first physiological state is a rest state and the second physiological state is an exercise state during which the subject is exercising.

Optionally, the first algorithm is based on a first set of biometric signals and the second algorithm is based on a second set of biometric signals; the second set of biometric signals being different from the first set of biometric signals.

Optionally, the second set of biometric signals comprises at least one more type of biometric signal than the first set of biometric signals.

Optionally, the first set of biometric signals consists essentially of the pulse wave signal.

Optionally, the second set of biometric signals and the first set of biometric signals are mutually exclusive.

Optionally, the first physiological state corresponds to a first pulse wave frequency measured in a first time interval having a value in a first range and the second physiological state corresponds to a second pulse wave frequency measured in the first time interval having a value in a second range; the second pulse wave frequency being higher than the first pulse wave frequency.

Optionally, the physiological state of the subject is classified based on a pulse wave frequency of the subject; and the processor is configured to control the one or more biometric sensors to detect one or more body motion signals when the physiological state of the subject is classified as the second physiological state based on the pulse wave frequency of the subject.

Optionally, the one or more biometric signals further comprise one or more body motion signals; and the physiological state of the subject is classified based on, at least in par the one or more body motion signals.

Optionally, the first physiological state corresponds to a first signal variation of at least one body motion signal measured in a second time interval having a value in a third range and the second physiological state corresponds to a second signal variation of the at least one body motion signal measured in the second time interval having a value in a fourth range; the second signal variation being larger than the first signal variation.

Optionally, the first signal variation and the second signal variation comprises art amplitude variation of the at least one body motion signal.

Optionally, the first signal variation and the second signal variation comprises it frequency variation of the at least one body motion signal.

Optionally, the first algorithm comprises calculating the heart rate based on the pulse wave signal alone.

Optionally, the second algorithm comprises fast Fourier transforming the second set of biometric signals to obtain at least a frequency spectrum of the pulse wave signal and a frequency spectrum of at least one body motion signal; processing the frequency spectrum of the pulse wave signal to generate a first composite signal comprising a first noise component and a pulse wave signal component; processing the frequency spectrum of the at least one body motion signal to generate a second composite signal comprising a second noise component; denoising the first composite signal based on the second noise component to generated a denoised signal; and calculating the heart rate based on the denoised signal.

Optionally, the one or more biosensors comprise at least one of a photoelectric sensor, a pressure sensor, an accelerometer, and barometer, and an image sensor.

Optionally, the apparatus further comprises an analog-to-digital converter configured to convert the one or more biometric signals into digital data, and transmit the digital data to the processor for analysis; and a user interface configured to display information and for a user to input data to the apparatus.

In another aspect, the present invention provides a wearable apparatus comprising the apparatus for determining the health parameter as described herein.

In another aspect, the present invention provides a method of determining a health parameter of a subject, comprising detecting one or more biometric signals of the subject comprising at least a pulse wave signal of the subject;

classifying physiological state of the subject as one of a plurality of physiological states comprising at least a first physiological state and a second physiological state based on the one or more biometric signals, the first physiological state being different from the second physiological state; and calculating the health parameter of the subject using one of a plurality of algorithms comprising at least a first algorithm corresponding to the first physiological state and a second algorithm corresponding to the second physiological state, the first algorithm being different from the second algorithm.

Optionally, the first physiological state is a rest state and the second physiological state is an exercise state during which the subject is exercising Optionally, the first algorithm is based on a first set of biometric signals and the second algorithm is based on a second set of biometric signals, the second set of biometric signals being different from the first set of biometric signals.

Optionally, the second set of biometric signals comprises at least one more type of biometric signal than the first set of biometric signals.

Optionally, the first set of biometric signals consists essentially of the pulse wave signal.

Optionally, the second set of biometric signals and the first set of biometric signals are mutually exclusive.

Optionally, the first physiological state corresponds to a first pulse wave frequency measured in a first time interval having a value in a first range and the second physiological state corresponds to a second pulse wave frequency measured in the first time interval having a value in a second range; the second pulse wave frequency being higher than the first pulse wave frequency.

Optionally, the physiological state of the subject is classified based on a pulse wave frequency of the subject; and the method further includes detecting one or more body motion signals when the physiological state of the subject is classified as the second physiological state based on the pulse wave frequency of the subject.

Optionally, the one or more biometric signals further comprise one or more body motion signals; and the physiological state of the subject is classified based on, at least in part, the one or more body motion signals.

Optionally, the first physiological state corresponds to a first signal variation of at least one body motion signal measured in a second time interval having a value in a third range and the second physiological state corresponds to a second signal variation of the at least one body motion signal measured in the second time interval having a value in a fourth range; the second signal variation being larger than the first signal variation.

Optionally, the first signal variation and the second signal variation comprises an amplitude variation of the at least one body motion signal.

Optionally, the first signal variation and the second signal variation comprises a frequency variation of the at least one body motion signal.

Optionally, the first algorithm comprises calculating the heart rate based on the pulse wave signal alone.

Optionally, the second algorithm comprises fast Fourier transforming the second set of biometric signals to obtain at least a frequency spectrum of the pulse wave signal and a frequency spectrum of at least one body motion signal; processing the frequency spectrum of the pulse wave signal to generate a first composite signal comprising a first noise component and a pulse wave signal component; processing the frequency spectrum of the at least one body motion signal to generate a second composite signal comprising a second noise component; denoising the first composite signal based on the second noise component to generated a denoised signal; and calculating the heart rate based on the denoised signal.

Optionally, the method further comprises converting the one or more biometric signals into digital data.

BRIEF DESCRIPTION OF THE FIGURES

The following drawings are merely examples for illustrative purposes according to various disclosed embodiments and are not intended to limit the scope of the present invention.

DETAILED DESCRIPTION

Figure 1:
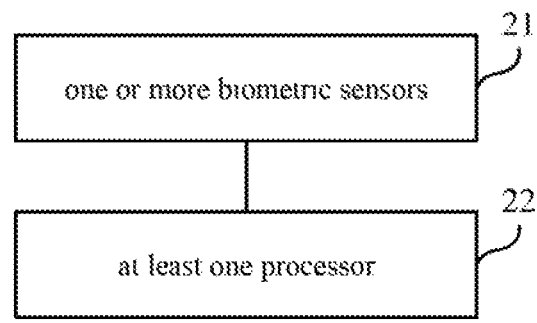
FIG. 1 is a schematic diagram illustrating the structure of an apparatus for determining a health parameter of a subject in some embodiments according to the present disclosure.

The disclosure will now be described more specifically with reference to the following embodiments. It is to be noted that the following descriptions of some embodiments are presented herein for purpose of illustration and description only. It is not intended to be exhaustive or to be limited to the precise form disclosed.

In conventional medical devices (e.g., a conventional wearable heart rate detector), a universal data sampling rate and a same calculation algorithm are used for calculating the health parameter of a subject regardless which physiological state the subject is in. For example, a conventional wearable heart rate detector calculates the heart rate of the subject using a same data sampling rate and a same calculation algorithm whether the subject is in a rest state or in an active state (e.g., an exercise state). When the subject is in the exercise state, in order to accurately determine the heart rate of the subject, it is necessary to denoise a pulse wave signal detected in the subject. Accordingly, the data sampling rate when the subject is in the exercise state is often higher, and the calculation algorithm used for calculating the heart rate more complicated, demanding higher computation resources and power consumption. It is discovered in the present disclosure that, when the subject is in a rest state, the pulse wave signal is relatively more stable. It is discovered in the present disclosure that, when the subject is in the rest state, it is not necessary to use a large data sampling rate and a complicated calculation algorithm. However, in the conventional heart rate detector, a same data sampling rate and a same calculation algorithm are used for calculating the heart rate regardless which physiological state (at rest or in exercise) the subject is in. The conventional heart rate detector requires higher computation resources and power consumption, resulting in a shortened battery life.

Accordingly, the present invention provides, inter alia, an apparatus and a method for determining a health parameter of a subject that substantially obviate one or more of the problems due to limitations and disadvantages of the related art. In one aspect, the present disclosure provides an apparatus for determining a health parameter of a subject. In some embodiments, the apparatus includes one or more biometric sensors configured to detect one or more biometric signals of the subject; a memory; at least one processor; wherein the one or more biometric sensors, the memory, the at least one processor are communicatively connected with each other. Optionally, the one or more biometric signals comprises at least a pulse wave signal. Optionally, the memory stores computer-executable instructions for controlling the at least one processor to receive the one or more biometric signals from the one or more biometric sensors; classify physiological state of the subject as one of a plurality of physiological states comprising at least a first physiological state and a second physiological state based on the one or more biometric signals, the first physiological state being different from the second physiological state; and calculate the health parameter of the subject using one of a plurality of algorithms comprising at least a first algorithm corresponding to the fir s t physiological state and a second algorithm corresponding to the second physiological state, the first algorithm being different from the second algorithm.

As used herein, the term "biometric signal" refers to a signal which is received from the one or more sensor. As used herein, the term "health parameter" refers to any parameter that gives information about the health of a subject. Optionally, the health parameter refers to a parameter which may be extracted or otherwise obtained by analyzing the one or more biometric signals. Examples of health parameters include, but are not limited to, a heart rate, a blood pressure, and the like.

FIG. 1 is a schematic diagram illustrating the structure of an apparatus for determining a health parameter of a subject in some embodiments according to the present disclosure. Referring to FIG. 1, the apparatus in some embodiments includes one or more biometric sensors 21 and at least one processor 22. The one or more biometric sensors 21 are configured to detect one or more biometric signals of the subject. Examples of biometric signals include both electrical biometric signals and non-electrical biometric signals. Examples of electrical biometric signals include, but are not limited to, an electrocardiogram signal, an electroencephalogram signal, an electromyogram signal, and the like. Examples of noon-electrical biometric signals include, but are not limited to, a body temperature signal, a blood pressure signal, a pulse wave signal, a body motion signal, and the like. Optionally, the one or more biometric signals includes at least a pulse wave signal of the subject. Examples of biosensors include, but are not limited to, a photoelectric sensor, a pressure sensor, an accelerometer, and barometer, and an image sensor. Examples of body motion signals include an acceleration signal of a body motion (e.g., detected by a three-axis acceleration sensor), a pressure signal (e.g., detected by a pressure sensor), an atmospheric pressure (e.g., detected by a barometer), and the like.

In some embodiments, the at least one processor 22 is configured to receive the one or more biometric signals from the one or more biometric sensors 21; classify physiological state of the subject as one of a plurality of physiological states including at least a first physiological state and a second physiological state based on the one or more biometric signals, the first physiological state being different from the second physiological state; and calculate the health parameter of the subject using one of a plurality of algorithms including at least a first algorithm corresponding to the first physiological state and a second algorithm corresponding to the second physiological state, the first algorithm being different from the second algorithm. Optionally, the first algorithm is based on a first set of biometric signals and the second algorithm is based on a second set of biometric signals; the second set of biometric signals being different from the first set of biometric signals. As used herein, the term "different" encompasses partly different or totally different. Optionally, the second set of biometric signals is different from the first set of biometric signals in that at least one biometric signal in the second set is absent in the first set. Optionally, the second set of biometric signals is different from the first set of biometric signals in that at least one biometric signal in the first set is absent in the second set. Optionally, the second set of biometric signals comprises at least one more type of biometric signal than the first set of biometric signals. Optionally, the first set of biometric signals consists essentially of the pulse wave signal. Optionally, the second set of biometric signals and the first set of biometric signals are mutually exclusive. Optionally, the first algorithm is different from the second algorithm in that they use different formulas for calculating the health parameter, whether or not they use a same set of biometric signals.

The processor may be configured to classify the physiological state of the subject as one of a plurality of physiological states, e.g., 2, 3, 4, 5, or more physiological states. For example, the first physiological state is a rest state and the second physiological state is an exercise state during which the subject is exercising. Various implementations may be practiced according to the present disclosure.

Optionally, the physiological state is a rest state. Examples of rest states of the subject include, but are not limited to, a sleeping state, a reclining state, a sitting state, an office work state, a reading state, a watching-TV state, and a leisure state.

Optionally, the physiological state is an exercise state. Optionally, the exercise state is an aerobic exercise state. Optionally, the exercise state is an anaerobic exercise state. Optionally, the exercise state is an ambulatory motion state such as a walking state, a running state, a hiking state, an interval training state, and a treadmill state. Optionally, the exercise state is a resistance training state.

In one example, the health parameter is a heart rate of the subject. The present apparatus first classifies the physiological state of the subject based on the biometric signals received from the one or more biometric sensors 21. If the physiological state of the subject is classified as a rest state, the heart rate may be calculated using a pulse wave signal of the subject alone, i.e., without using other biometric signals. If the physiological state of the subject is classified as an exercise state, the heart rate is calculated using a combination of biometric signals, e.g., a combination of a pulse wave signal and one or more body motion signals.

In some embodiments, the processor 22 is configured to classify the physiological state of the subject based on the pulse wave signal received from the one or more biometric sensors 21. Optionally, the first physiological state corresponds to a first pulse wave frequency measured in a first time interval having a value in a first range and the second physiological state corresponds to a second pulse wave frequency measured in the first time interval having a value in a second range; the second, pulse wave frequency being higher than the first pulse wave frequency. In one example, if the pulse wave frequency measured in the first time interval having a value equals to or greater than a first threshold value, the physiological state of the subject is classified as the second physiological state, e.g., an exercise state. In another example, if the pulse wave frequency measured in the first time interval having a value less than the first threshold value, the physiological state of the subject is classified as the first physiological state, e.g., a rest state.

Pulse wave signals of the subject may be detected by various pulse wave sensors. Typically, pulse wave signal is represented in a wave form having an amplitude. Depending on the pulse wave sensor used for detecting the pulse wave signal and the method used for converting the pulse wave signal, the amplitude may be represented by a different value. By measuring the pulse wave frequency of the pulse wave, the physiological state of the subject may be determined independent from the amplitude value. Typically, the pulse wave frequency of an adult is in the range of approximately 60 times per minute to approximately 100 times per minute. The threshold value may be set to distinguish different physiological states suitable for various implementations.

In another example, the pulse wave frequency may be used for classifying the physiological state of the subject as one of a rest state, an aerobic exercise state, and an anaerobic exercise state. The rest state corresponds to a first pulse wave frequency measured in a first time interval having a value in a first range, the anaerobic exercise state corresponds to a second pulse wave frequency measured in the first time interval having a value in a second range, and the aerobic exercise state corresponds to a third pulse wave frequency measured in the first time interval having a value in a third range. The third pulse wave frequency is higher than the second pulse wave frequency, which is in turn higher than the first pulse wave frequency.

In some embodiments, the processor 22 is configured to classify the physiological state of the subject based on one or more body motion signals received from the one or more biometric sensors 21. Optionally, the first physiological state corresponds to a first signal variation of at least one body motion signal measured in a second time interval having a value in a third range and the second physiological state corresponds to a second signal variation of the at least one body motion signal measured in the second time interval having a value in a fourth range; the second signal variation being larger than the first signal variation. In one example, if the signal variation of at least one or more body motion signals measured in the second time interval having a value equals to or greater than a second threshold value, the physiological state of the subject is classified as the second physiological state, e.g., an exercise state. In another example, if the signal variation of at least one or more body motion signals measured in the second time interval, having a value less than the second threshold value, the physiological state of the subject is classified as the first physiological state, e.g., a rest state. Optionally, the signal variation is an amplitude variation of the at least one body motion signal. Optionally, the signal variation is a frequency variation of the at least one body motion signal.

In another example, the signal variation of at least one or more body motion signals may be used for classifying the physiological state of the subject as one of a rest state, an aerobic exercise state, and an anaerobic exercise state. The rest state corresponds to a first signal variation of at least one or more body motion signals measured in a second time interval having a value in a first range, the anaerobic exercise state corresponds to a second signal variation of at least one or more body motion signals measured in the second time interval having a value in a second range, and the aerobic exercise state corresponds to a third signal variation of at least one or more body motion signals measured in the first time interval having a value in a third range. The third signal variation of at least one or more body motion signals is higher than the second signal variation of at least one or more body motion signals, which is in turn higher than the first signal variation of at least one or more body motion signals.

In some embodiments, the processor 22 is configured to classify the physiological state of the subject based on a combination of the pulse wave signal and one or more body motion signals received from the one or more biometric sensors 21.

Once the physiological state of the subject is classified, the health parameter of the subject may be calculated using different algorithms for different physiological states. For example, a first algorithm may be used for calculating the health parameter for the subject in a first physiological state, and a different, second algorithm may be used for calculating the health parameter of the subject in a second physiological state. In one example, the first physiological state is a rest state and the second physiological state is an exercise state. Optionally, the first algorithm demands less computation power as compared to the second algorithm, thus the first algorithm demands less power consumption of the apparatus. Different algorithms may use different sets of biometric signals for computation. Optionally, different algorithms may use different formulas for calculating the health parameter. In one example, the first algorithm uses a pulse wave signal alone for calculating the health parameter (e.g., a heart rate of the subject) for a subject in a rest state. In another example, the second algorithm uses a set of biometric signals currently detected by the one or more biometric sensors including the pulse wave signal for calculating the health parameter for a subject in an exercise state.

In one example, the health parameter is a heart rate of the subject, and the first algorithm includes calculating the heart rate based on the pulse wave signal alone. Optionally, the first algorithm includes processing the pulse wave signal to ascertain peaks and valleys of the pulse wave and intervals between adjacent peaks or intervals between adjacent valleys thereby obtaining an amplitude variation curve having a plurality of peaks, valleys, and intervals. The first algorithm further includes calculating the heart rate based on the amplitude variation curve. The first algorithm uses only a pulse wave signal, thus demands less computation resources and less power consumption.

Optionally, the first algorithm is used for calculating the heart rate (or other appropriate health parameters such as a blood pressure) of a subject in a rest state. Optionally, the first algorithm is used for calculating the heart rate (or other appropriate health parameters such as a blood pressure) of a subject when only biometric signal being detected is the pulse wave signal.

Optionally, the heart rate of a subject in a rest state may be calculated using a simple method by measuring the number of heart beats of the subject in a certain time interval.

In another example, the health parameter is a heart rate of the subject, and the second algorithm includes fast Fourier transforming the second set of biometric signals detected in real time to obtain at least a frequency spectrum of the pulse wave signal and a frequency spectrum of at least one body motion signal; processing the frequency spectrum of the pulse wave signal to generate a first composite signal including a first noise component and a pulse wave signal component; processing the frequency spectrum of the at least one body motion signal to generate a second composite signal comprising a second noise component, denoising the first composite signal based on the second noise component to generated a denoised signal; and calculating the heart rate based on the denoised signal.

Optionally, the second algorithm is used for calculating the heart rate (or other appropriate health parameters such as a blood pressure) of a subject in an exercise state.

Optionally, the at least one processor 21 is any one of or a combination of a central processor, a single-chip microcontroller, a micro control unit, a digital signal processor, and an advance RISC machines (ARM) processor.

Figure 2:
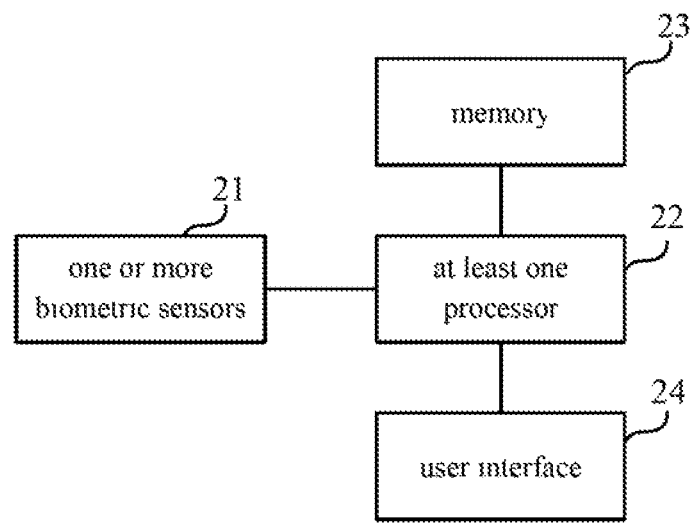
FIG. 2 is a schematic diagram illustrating the structure of an apparatus for determining a health parameter of a subject in some embodiments according to the present disclosure.

FIG. 2 is a schematic diagram illustrating the structure of an apparatus for determining a health parameter of a subject in some embodiments according to the present disclosure. Referring to FIG. 2, the apparatus in some embodiments includes one or more biometric sensors 21, at least one processor 22, a memory 23, and a user interface 24. Thus, the apparatus in some embodiments additionally has a display function, a storage function, and an alert function. The one or more biometric sensors 21, the memory 23, the user interface 24, and the at least one processor 22 are communicatively connected with each other.

Optionally, the memory 23 is configured to store data corresponding to the one or more biometric signals detected by the one or more biometric sensors 21, and data generated by the at least one processor 22 (e.g., health parameters such as a heart rate, physiological states, etc.).

Optionally, the user interface 24 (e.g., a display) is configured to display data corresponding to the one or more biometric signals detected by the one or more biometric sensors 21, and data generated by the at least one processor 22 (e.g., health parameters such as a heart rate, physiological states, etc.).

Optionally, the memory 23 is any one or a combination of a random-access memory, a read-only memory, and a magnetic disk.

Optionally, the biometric signal detected by the one or more biometric sensors 21 is a digital signal. Optionally, the biometric signal detected by the one or more biometric sensors 21 is an analog signal. Optionally, the analog signal may be first converted into a digital signal before it is transmitted to the processor 22.

Figure 3:
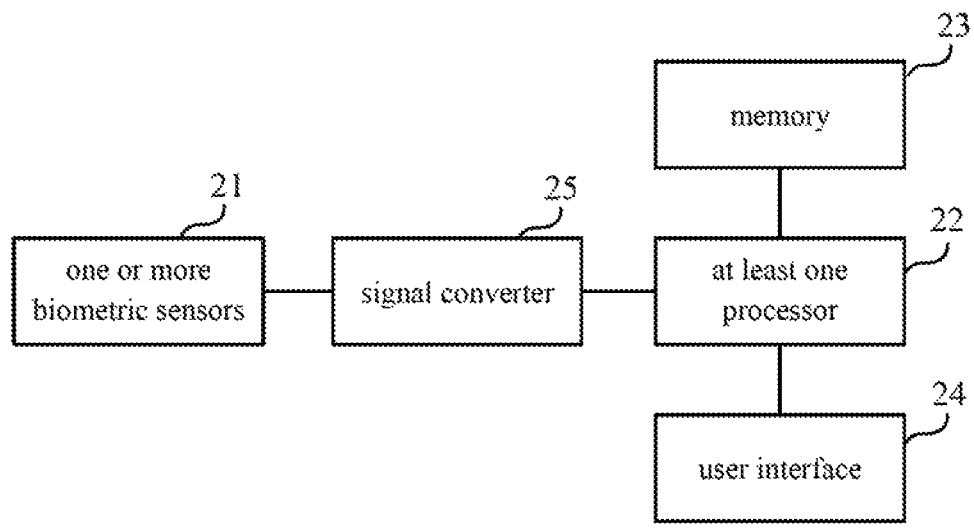
FIG. 3 is a schematic diagram illustrating the structure of an apparatus for determining a health parameter of a subject in some embodiments according to the present disclosure.

FIG. 3 is a schematic diagram illustrating the structure of an apparatus for determining a health parameter of a subject in some embodiments according to the present disclosure. Referring to FIG. 3, the apparatus in some embodiments includes one or more biometric sensors 21, at least one processor 22, a memory 23, a user interface 24, and a signal converter 25. Optionally, the signal converter 25 is an analog-to-digital converter. The analog-to-digital converter is configured to convert an analog signal into a digital signal when one or more biometric signal detected by the one or more biometric sensors 21 is in an analog form.

Optionally, the signal converter is any one or a combination of an analog-to-digital conversion chip, an analog-to-digital conversion circuit, and a circuit board having an analog to-digital conversion chip or an analog-to-digital conversion circuit.

In the present apparatus (e.g., the apparatuses of FIGS. 1 to 3), the physiological state of the subject may be classified based on, alone or in combination, the pulse wave signal, one or more body motion signals, as well as other biometric signals detected by the one or more biometric sensors 21. In some embodiments, the physiological state of the subject is first classified based on one biometric signal, once the physiological state is classified as the second physiological state (e.g., an exercise state), the processor may be configured to control the one or more biometric sensors 21 to detect additional biometric signals, e.g., body motion signals, temperature sings, electroencephalogram signals. Optionally, the one or more biometric sensor 21 detect a plurality of biometric signals including the pulse wave signal, but only the pulse wave signal is used in classification of the physiological state of the subject. Optionally, the one or more biometric sensor 21 only detect the pulse wave signal at the initial stage (e.g., when classifying the physiological state of the subject), once the physiological state is classified as the second physiological state (e.g., an exercise state), the processor 22 may be configured to control the one or more biometric sensors 21 to detect additional biometric signals, e.g., body motion signals, temperature signals, electroencephalogram signals. By having this design, the demand of computation resources and power consumption placed on the apparatus may be further reduced.

Figure 4:
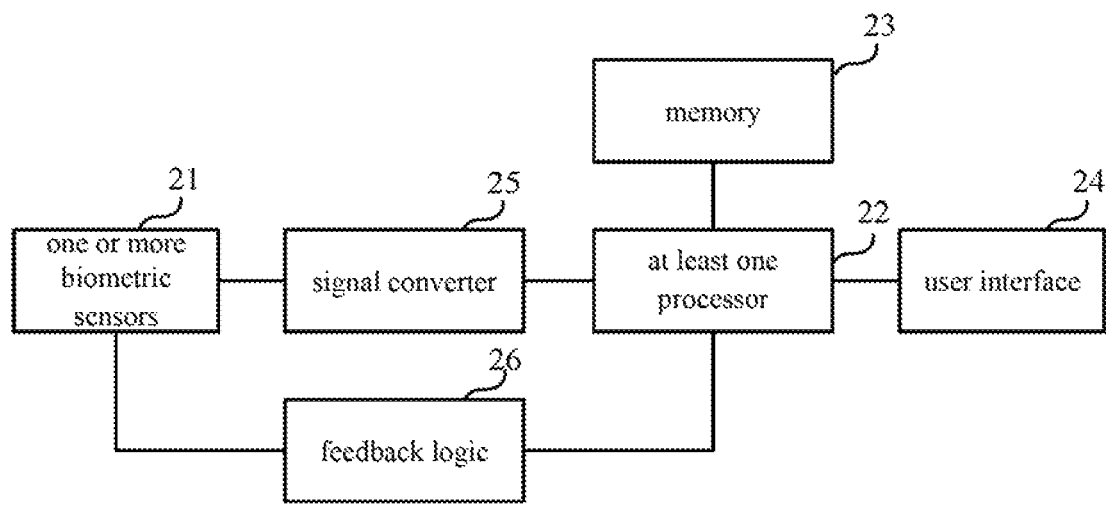
FIG. 4 is a schematic diagram illustrating the structure of an apparatus for determining a health parameter of a subject in some embodiments according to the present disclosure.

FIG. 4 is a schematic diagram illustrating the structure of an apparatus for determining a health parameter of a subject in some embodiments according to the present disclosure. Referring to FIG. 4, the apparatus in some embodiments includes one or more biometric sensors 21, at least one processor 22, a memory 23, a signal converter 25, a user interface 24, and a feedback logic 26. The feedback logic 26 is configured to feedback the current physiological state of the subject to the one or more biometric sensors 21, and control the one or more biometric sensors 21 to detect additional biometric signals (e.g., one or more body motion signals) when the physiological state of the subject is classified as the second physiological state based on a first set of biometric signals (e.g., the pulse wave frequency of the subject). By having a feedback mechanism, the demand of computation resources and power consumption placed on the apparatus be further reduced.

Figure 5:
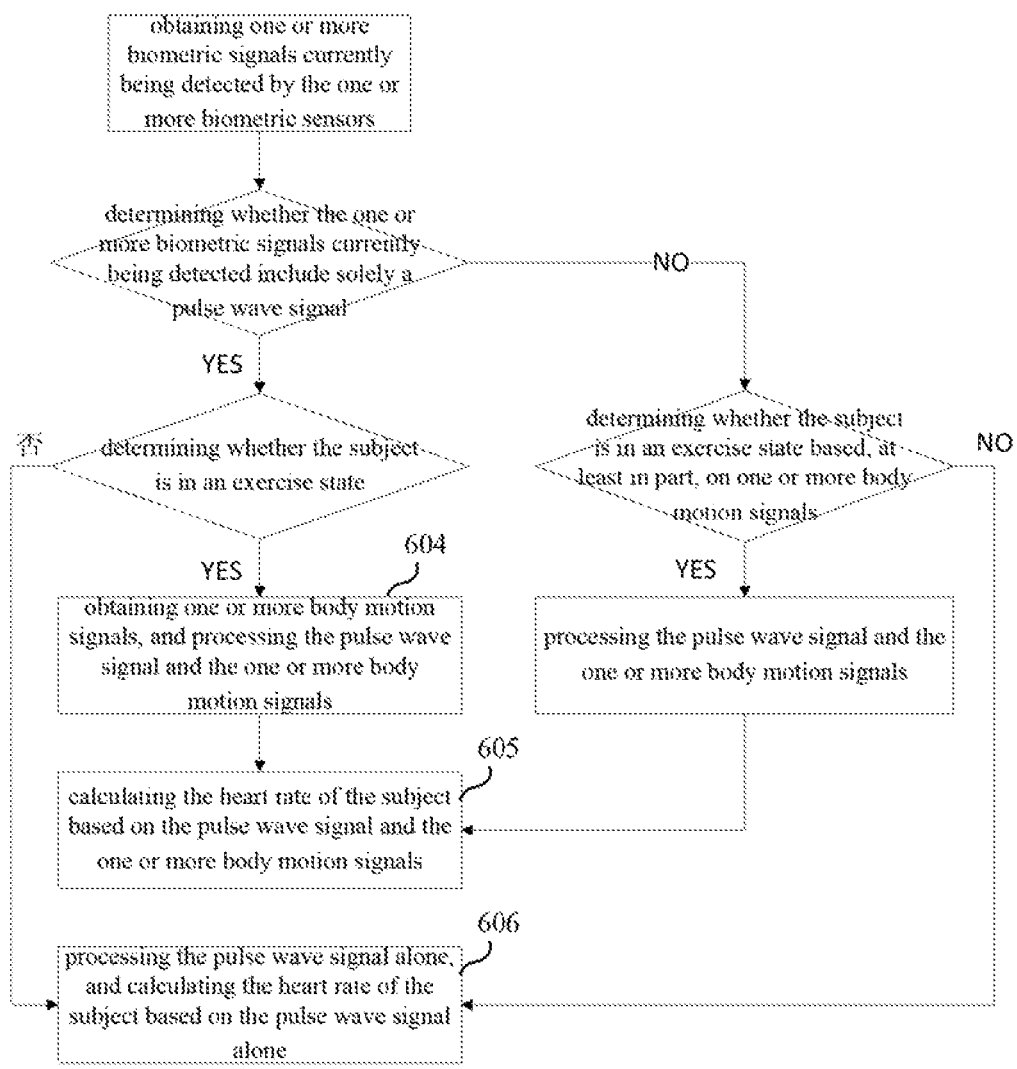
FIG. 5 is a flow chart illustrating a process of determining a heart rate of a subject in some embodiments according to the present disclosure.

FIG. 5 is a flow chart illustrating a process of determining a heart rate of a subject in some embodiments according to the present disclosure. Referring to FIG. 5, the process includes first obtaining one or more biometric signals currently being detected by the one or more biometric sensors. For example, the one or more biometric signals currently being detected may be detected by the one or more biometric sensors 21 as shown in FIG. 4. Optionally, the one or more biometric signals currently being detected include only a pulse wave signal. Optionally, the one or more biometric signals currently being detected include a pulse wave signal and one or more body motion signal. Optionally, the one or more biometric signals currently being detected include a pulse wave signal and one or more biometric signals (other than the one or more body motion signals). The process in FIG. 5 uses the pulse wave signal and one or more body motion signals for illustration, other biometric signals may be used in lieu of the pulse wave signal or in lieu of the one or more body motion signals.

In some embodiments, the process further includes determining whether the one or more biometric signals currently being detected include solely a pulse wave signal. For example, the determination may be performed by the at least one processor 22 as shown in FIG. 4. Optionally, the determination may be performed based on an indication signal transmitted by the one or more biometric sensors.

If the one or more biometric signals currently being detected include solely a pulse wave signal, the process further includes determining whether the subject is in an exercise state. If the subject is determined to be in an exercise state, the process further includes obtaining one or more body motion signals, and processing the pulse wave signal and the one or more body motion signals. Because the subject is determined to be in the exercise state, it is necessary to denoise the pulse wave signal in order to determine a heart rate of the subject more accurately. In order to denoise the pulse wave signal, another biometric signal such as a body motion signal is needed to perform the denoising function. For example, the feedback logic 25 as shown in FIG. 4 may be used to feedback the physiological state of the subject to the one or more biometric sensors 21, and control the one or more biometric sensors 21 to detect the one or more body motion signals. Once the one or more body motion signals and the pulse wave signal are obtained, the process further includes calculating the heart rate of the subject based on the pulse wave signal and the one or more body motion signals.

If the one or more biometric signals currently being detected are determined to include a pulse wave signal, and the subject is determined to be in a rest state, the process further includes processing the pulse wave signal alone, and calculating the heart rate of the subject based on the pulse wave signal alone.

If the one or more biometric signals currently being detected include the pulse wave signal and one or more additional biometric signals (e.g., one or more body motion signals), the process may include determining whether the subject is in an exercise state based, at least in part, on one or more body motion signals. If the subject is determined to be in an exercise state, the process further includes processing the pulse wave signal and the one or more body motion signals, and calculating the heart rate of the subject based on the pulse wave signal and the one or more body motion signals. If the subject is determined to be in a rest state, the process further includes processing the pulse wave signal alone, and calculating the heart rate of the subject based on the pulse wave signal alone.

In performing various steps of the process, various data and parameters may be stored in a memory, e.g., a memory 23 as shown in FIG. 4. Examples of data and parameters that may be stored in the memory include various wave parameters, results of processing the pulse wave signal and one or more body motion signals, the calculated heart rates. Various data and parameters may be display on a user interface, e.g., a user interface 24 as shown in FIG. 4. When the one or more biometric signals are in an analog form, they may be first converted in to a digital form by a signal converter, e.g., the signal converter 25 as shown in FIG. 4.

The present apparatus processes biometric signals in different processing modes depending on different physiological states of the subject, different processing modes place different demand on computation resources and power consumption. The battery life of the apparatus may be extended as compared to a conventional apparatus.

Figure 6:
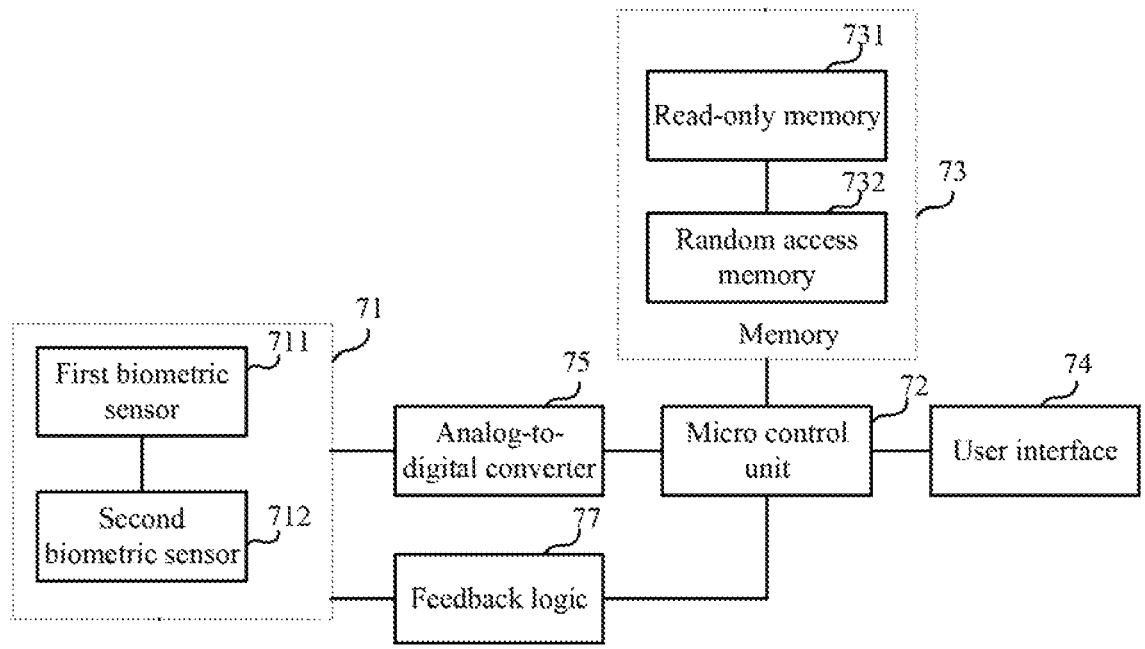
FIG. 6 is a schematic diagram illustrating the structure of a wearable apparatus for determining a health parameter of a subject in some embodiments according to the present disclosure.

In another aspect, the present disclosure provides a wearable apparatus. FIG. 6 a schematic diagram illustrating the structure of a wearable apparatus for determining a health parameter of a subject in some embodiments according to the present disclosure. Referring to FIG. 6, the wearable apparatus in some embodiments includes one or more biometric sensors 71 including at least a first biometric sensor 711 and a second biometric sensor 712. For example, the first biometric sensor 711 is configured to detect a pulse wave signal of a subject, and the second biometric sensor 712 is configured to detect one or more body motion signals of the subject. The wearable apparatus in some embodiments further includes a micro control unit 72 configured to receive the one or more biometric signals from the one or more biometric sensors 71, classify physiological state of the subject as one of a plurality of physiological states including at least a first physiological state and a second physiological state based on the one or more biometric signals, the first physiological state being different from the second physiological state, and calculate the health parameter of the subject using one of a plurality of algorithms including at least a first algorithm corresponding to the first physiological state and a second algorithm corresponding to the second physiological state, the first algorithm being different from the second algorithm. For example, the micro control unit 72 is configured to determine the physiological state of the subject based on the pulse wave signal and one or more body motion signals, and select a different processing mode corresponding to a different physiological state. In one example, the subject is in an exercise state, the micro control unit 72 is configured to calculate the heart rate based on a combination of the pulse wave signal and the one or more body motion signals. In another example, the subject is in a rest state, the micro control unit 72 is configured to calculate the heart rate solely based on the pulse wave signal. The wearable apparatus in some embodiments further includes a memory 73 including at least a read-only memory 731 and a random-access memory 732. The memory 73 is configured to store various data and parameters such as the pulse wave signal, the one or more body motion signals, and the heart rate. The random-access memory 732 may also provide cache assistance for the micro control unit 72 to speed up the processing speed of the micro control unit 72. The wearable apparatus in some embodiments further includes a user interface 74 configured to display various data and parameters such as the pulse wave signal, the one or more body motion signals, and the heart rate, as well as other information. Examples of wearable apparatuses include, but are not limited to, a smart watch, an electronic ring, an electronic necklace, an electronic bracelet, an electronic badge, an electronic fitness monitoring device, a smart wristband, an electronic hat, smart glasses, a wearable apparatus that is worn on clothing, a wearable apparatus that when worn contacts human skin.

The wearable apparatus in some embodiments further includes an analog-to-digital converter 75 configured to convert biometric signals in an analog form into a digital form, and transmit the digital data to the micro control unit 72.

The wearable apparatus in some embodiments further includes a feedback logic 77 configured to feedback the physiological state of the subject to the one or more biometric sensors 71, and control to the one or more biometric sensors 72 to detect additional biometric signals such as one or more body motion signals. By having the feedback logic 77, the one or more biometric sensors 71 may be configured to detect only the pulse wave signal at the initial stage, and upon receiving the feedback signal from the feedback logic 77, the one or more biometric sensors 71 is configured to detect additional biometric signals. This design places less burden of computation resources and power consumption on the wearable apparatus.

The wearable apparatus in some embodiments further includes a power supply configured to provide power to the wearable apparatus.

The present wearable apparatus processes biometric signals in different processing modes depending on different physiological states of the subject, different processing modes place different demand on computation resources and power consumption. In the present wearable apparatus, the battery life may be extended as compared to a conventional wearable apparatus.

Figure 7:
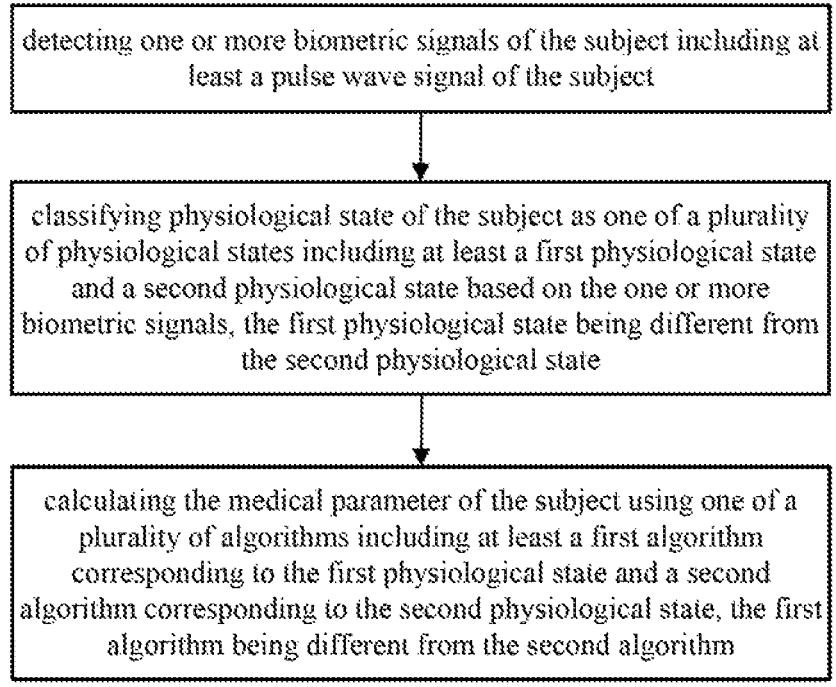
FIG. 7 is a flow chart illustrating a method of determining a health parameter of a subject some embodiments according to the present disclosure.

In another aspect, the present disclosure further provides a method of determining a health parameter of a subject. FIG. 7 is a flow chart illustrating a method of determining a health parameter of a subject in some embodiments according to the present disclosure. Referring to FIG. 7, the method in some embodiments includes detecting one or more biometric signals of the subject including at least a pulse wave signal of the subject; classifying physiological state of the subject as one of a plurality of physiological states including at least a first physiological state and a second physiological state based on the one or more biometric signals, the first physiological state being different from the second physiological state; and calculating the health parameter of the subject using one of a plurality of algorithms including at least a First algorithm corresponding to the first physiological state and a second algorithm corresponding to the second physiological state, the first algorithm being different from the second algorithm. Examples of biometric signals include both electrical biometric signals and non-electrical biometric signals. Examples of electrical biometric signals include, but are not limited to, an electrocardiogram signal, an electroencephalogram signal, an electromyogram signal, and the like. Examples of noon-electrical biometric signals include, but are not limited to, a body temperature signal, a blood pressure signal, a pulse wave signal, a body motion signal, and the like. Optionally, the one or more biometric signals includes at least a pulse wave signal of the subject. Examples of body motion signals include an acceleration signal of a body motion (e.g., detected by a three-axis acceleration sensor), a pressure signal (e.g., detected by a pressure sensor), an atmospheric pressure (e.g., detected by a barometer), and the like.

Optionally, the first algorithm is based on a first set of biometric signals and the second algorithm is based on a second set of biometric signals; the second set of biometric signals being different from the first set of biometric signals. Optionally, the second set of biometric signals comprises at least one more type of biometric signal than the first set of biometric signals. Optionally, the first set of biometric signals consists essentially of the pulse wave signal. Optionally, the second set of biometric signals and the first set of biometric signals are mutually exclusive.

Optionally, the method includes classifying the physiological state of the subject as one of a plurality of physiological states, e.g., 2, 3, 4, 5, or more physiological states. For example, the first physiological state is a rest state and the second physiological state is an exercise state during which the subject is exercising.

In one example, the health parameter is a heart rate of the subject. The present method includes first classifying the physiological state of the subject based on the biometric signals currently being detected. If the physiological state of the subject is classified as a rest state, the heart rate may be calculated using a pulse wave signal of the subject alone, i.e., without using other biometric signals. If the physiological state of the subject is classified as an exercise state, the heart rate is calculated using a combination of biometric signals, e.g., a combination of a pulse wave signal and one or more body motion signals.

In some embodiments, the present method includes classifying the physiological state of the subject based on the pulse wave signal. Optionally, the first physiological state corresponds to a first pulse wave frequency measured in a first time interval having a value in a first range and the second physiological state corresponds to a second pulse wave frequency measured in the first time interval having a value in a second range; the second pulse wave frequency being higher than the first pulse wave frequency. In one example, if the pulse wave frequency measured in the first time interval having a value equals to or greater than a first threshold value, the physiological state of the subject is classified as the second physiological state, e.g., an exercise state. In another example, if the pulse wave frequency measured in the first time interval having a value less than the first, threshold value, the physiological state of the subject is classified as the first physiological state, e.g., a rest state.

In some embodiments, the present method includes classifying the physiological state of the subject based on one or more body motion signals. Optionally, the first physiological state corresponds to a first signal variation of at least one body motion signal measured in a second time interval having a value in a third range and the second physiological state corresponds to a second signal variation of the at least one body motion signal measured in the second time interval having a value in a fourth range; the second signal variation being larger than the first signal variation. In one example, if the signal variation of at least one or more body motion signals measured in the second time interval having a value equals to or greater than a second threshold value, the physiological state of the subject is classified as the second physiological state, e.g., an exercise state. In another example, if the signal variation of at least one or more body motion signals measured in the second time interval having a value less than the second threshold value, the physiological state of the subject is classified as the first physiological state, e.g., a rest state. Optionally, the signal variation is an amplitude variation of the at least one body motion signal. Optionally, the signal variation is a frequency variation of the at least one body motion signal.

In some embodiments, the present method includes classifying the physiological state of the subject based on a combination of the pulse wave signal and one or more body motion signals.

Once the physiological state of the subject is classified, the health parameter of the subject may be calculated using different algorithms corresponding to different physiological states. For example, a first algorithm may be used for calculating the health parameter for the subject in a first physiological state, and a different, second algorithm may be used for calculating the health parameter of the subject in a second physiological state. In one example, the first physiological state is a rest state and the second physiological state is an exercise state. In one example, the first algorithm uses a pulse wave signal alone for calculating the health parameter (e.g., a heart rate of the subject) for a subject in a rest state. In another example, the second algorithm uses a set of biometric signals currently detected by the one or more biometric sensors including the pulse wave signal for calculating the health parameter for a subject in an exercise state.

In one example, the health parameter is a heart rate of the subject, and the first algorithm includes calculating the heart rate based on the pulse wave signal alone. Optionally, the first algorithm includes processing the pulse wave signal to ascertain peaks and valleys of the pulse wave and intervals between adjacent peaks or intervals between adjacent valleys thereby obtaining an amplitude variation curve having a plurality of peaks, valleys, and intervals. The first algorithm further includes calculating, the heart rate based on the amplitude variation curve. The first algorithm uses only a pulse wave signal, thus demands less computation resources and less power consumption.

Optionally, the first algorithm is used for calculating the heart rate (or other appropriate health parameters such as a blood pressure) of a subject in a rest state. Optionally, the first algorithm is used for calculating the heart rate (or other appropriate health parameters such as a blood pressure) of a subject when only biometric signal being detected is the pulse wave signal.

In another example, the health parameter is a heart rate of the subject, and the second algorithm includes fast Fourier transforming the second set of biometric signals detected in real time to obtain at least a frequency spectrum of the pulse wave signal and a frequency spectrum of at least one body motion signal; processing the frequency spectrum of the pulse wave signal to generate a first composite signal including a first noise component and a pulse wave signal component; processing the frequency spectrum of the at least one body motion signal to generate a second composite signal comprising a second noise component; denoising the first composite signal based on the second noise component to generated a denoised signal; and calculating the heart rate based on the denoised signal.

Optionally, the second algorithm is used for calculating the heart rate (or other appropriate health parameters such as a blood pressure) of a subject in an exercise state.

In some embodiments, the physiological state of the subject is classified based on a pulse wave frequency of the subject, and the method further includes detecting one or more body motion signals when the physiological state of the subject is classified as the second physiological state based on the pulse wave frequency of the subject.

In some embodiments, the one or more biometric signals currently being detected further includes one or more body motion signals, and the physiological state of the subject is classified based on, at least in part, the one or more body motion signals.

The foregoing description of the embodiments of the invention has been presented for imposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. An apparatus for determining a health parameter of a subject, comprising:
    one or more biometric sensors configured to detect one or more biometric signals of the subject;
    a memory; and
    at least one processor;
    wherein the one or more biometric sensors, the memory, the at least one processor are communicatively connected with each other;
    the one or more biometric signals comprises at least a pulse wave signal of the subject; and
    the memory stores computer-executable instructions for controlling the at least one processor to:
    receive the one or more biometric signals from the one or more biometric sensors;
    classify physiological state of the subject as one of a plurality of physiological states comprising a rest state, a running state, and a walking state based on the one or more biometric signals; and
    calculate the health parameter of the subject using one of a plurality of algorithms comprising at least a first algorithm corresponding to the rest state and a second algorithm corresponding to the running state or the walking state, the first algorithm being different from the second algorithm;
    wherein the first algorithm comprises calculating a first heart rate based on a first pulse wave signal alone;
    wherein calculating the first heart rate based on the first pulse wave signal alone comprises processing the pulse wave signal to obtain an amplitude variation curve having a plurality of peaks, valleys, and intervals; and calculating the heart rate based on the amplitude variation curve;
    wherein the second algorithm comprises:
    fast Fourier transforming a second pulse wave signal to obtain a frequency spectrum of the second pulse wave signal and fast Fourier transforming at least one body motion signal other than the second pulse wave signal to obtain a frequency spectrum of the at least one body motion signal other than the second pulse wave signal;
    processing the frequency spectrum of the second pulse wave signal to generate a first composite signal comprising a first noise component and a pulse wave signal component;
    processing the frequency spectrum of the at least one body motion signal to generate a second composite signal comprising a second noise component;
    denoising the first composite signal based on the second noise component to generate a denoised signal; and
    calculating a second heart rate based on the denoised signal.

2. The apparatus of claim 1, wherein the one or more biometric sensors comprise at least one of a photoelectric sensor, a pressure sensor, an accelerometer, and barometer, or an image sensor.

3. The apparatus of claim 1, further comprising an analog-to-digital converter configured to convert the one or more biometric signals into digital data, and transmit the digital data to the processor for analysis; and
  a user interface configured to display information and for a user to input data to the apparatus.

4. A wearable apparatus, comprising the apparatus for determining the health parameter of claim 1.

5. A method of determining a health parameter of a subject, comprising:
  detecting one or more biometric signals of the subject comprising at least a pulse wave signal of the subject;
  classifying physiological state of the subject as one of a plurality of physiological states comprising a rest state, a running state, and a walking state based on the one or more biometric signals; and
  calculating the health parameter of the subject using one of a plurality of algorithms comprising at least a first algorithm corresponding to the rest state and a second algorithm corresponding to the running state or the walking state, the first algorithm being different from the second algorithm;
  wherein the first algorithm comprises calculating a first heart rate based on a first pulse wave signal alone;
  wherein calculating the first heart rate based on the first pulse wave signal alone comprises processing the pulse wave signal to obtain an amplitude variation curve having a plurality of peaks, valleys, and intervals; and calculating the heart rate based on the amplitude variation curve;
  wherein the second algorithm comprises:
  fast Fourier transforming a second pulse wave signal to obtain a frequency spectrum of the second pulse wave signal and fast Fourier transforming at least one body motion signal other than the second pulse wave signal to obtain a frequency spectrum of the at least one body motion signal other than the second pulse wave signal;
  processing the frequency spectrum of the second pulse wave signal to generate a first composite signal comprising a first noise component and a pulse wave signal component;
  processing the frequency spectrum of the at least one body motion signal to generate a second composite signal comprising a second noise component;
  denoising the first composite signal based on the second noise component to generate a denoised signal; and
  calculating a second heart rate based on the denoised signal.

* * * * *